(12) United States Patent
Ellis et al.

(10) Patent No.: US 9,909,165 B2
(45) Date of Patent: Mar. 6, 2018

(54) NUCLEIC ACID PREPARATION METHOD

(71) Applicant: LIFE TECHNOLOGIES AS, Oslo (NO)

(72) Inventors: Darren Ellis, Lommedalen (NO); Geir Fonnum, Fjellhamar (NO); Nini Kjus, Oslo (NO)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/431,678

(22) Filed: Feb. 13, 2017

(65) Prior Publication Data
US 2017/0204398 A1 Jul. 20, 2017

Related U.S. Application Data

(62) Division of application No. 13/989,782, filed as application No. PCT/EP2011/071218 on Nov. 28, 2011, now Pat. No. 9,708,645.

(60) Provisional application No. 61/421,523, filed on Dec. 9, 2010.

(30) Foreign Application Priority Data

Nov. 26, 2010 (GB) .................................. 1020095.4

(51) Int. Cl.
C12Q 1/68 (2006.01)
C12N 15/10 (2006.01)

(52) U.S. Cl.
CPC ....... *C12Q 1/6806* (2013.01); *C12N 15/1013* (2013.01)

(58) Field of Classification Search
CPC .................................................. C12Q 1/6806
USPC ......................................................... 435/6.1
See application file for complete search history.

(56) References Cited

U.S. PATENT DOCUMENTS

| 5,705,628 | A | 1/1998 | Hawkins |
| 5,898,071 | A | 4/1999 | Hawkins |
| 6,342,387 | B1 | 1/2002 | Hayashizaki et al. |
| 6,355,792 | B1 | 3/2002 | Michelsen et al. |
| 6,936,414 | B2 | 8/2005 | Gundling |
| 7,491,495 | B2 | 2/2009 | Zielenski et al. |
| 7,888,006 | B2 | 2/2011 | Lenz |
| 8,222,397 | B2 | 7/2012 | Bitner |
| 8,247,545 | B1 | 8/2012 | Colpan |
| 8,598,338 | B2 | 12/2013 | Bair et al. |
| 8,624,020 | B2 | 1/2014 | Himmelreich et al. |
| 2002/0110829 | A1 | 8/2002 | Kolzau et al. |
| 2004/0137449 | A1 | 7/2004 | Nargessi |
| 2006/0147944 | A1 | 7/2006 | Chomezynski |
| 2009/0069554 | A1 | 3/2009 | Finne |
| 2011/0224419 | A1 | 9/2011 | Himmelreich |

FOREIGN PATENT DOCUMENTS

| EP | 0796327 | 7/2004 |
| EP | 1804045 | 7/2007 |
| EP | 2163621 | 3/2010 |
| EP | 2264184 | 12/2010 |
| EP | 2295567 | 11/2013 |
| WO | WO-1991/012079 | 8/1991 |
| WO | WO-1996/009379 | 3/1996 |
| WO | WO-2006/079660 | 8/2006 |
| WO | WO-2008/097342 | 8/2008 |
| WO | WO-2010/026167 | 3/2010 |
| WO | WO-2011/026028 | 3/2011 |
| WO | WO-2011/083429 | 7/2011 |
| WO | WO-2012/069660 | 5/2012 |

OTHER PUBLICATIONS

GB1020095.4, "Search Report dated Mar. 25, 2011", 4 Pages.
PCT/EP2011/071218, "International Search Report and Written Opinion dated Feb. 24, 2012", 8 Pages.

*Primary Examiner* — Jezia Riley

(57) ABSTRACT

A method for processing a nucleic acid, in which the nucleic acid is exposed to an aqueous medium which includes a polyol in sufficient proportion for at least a portion of the nucleic acid to enter or remain in an extra-solution phase. Thus, a polyol may be used to bind a nucleic acid which is in solution to a solid support or to wash a nucleic acid on a solid support while maintaining it on the support. The polyol may for example be a $C_2$-$C_{10}$ alkanediol.

8 Claims, 7 Drawing Sheets

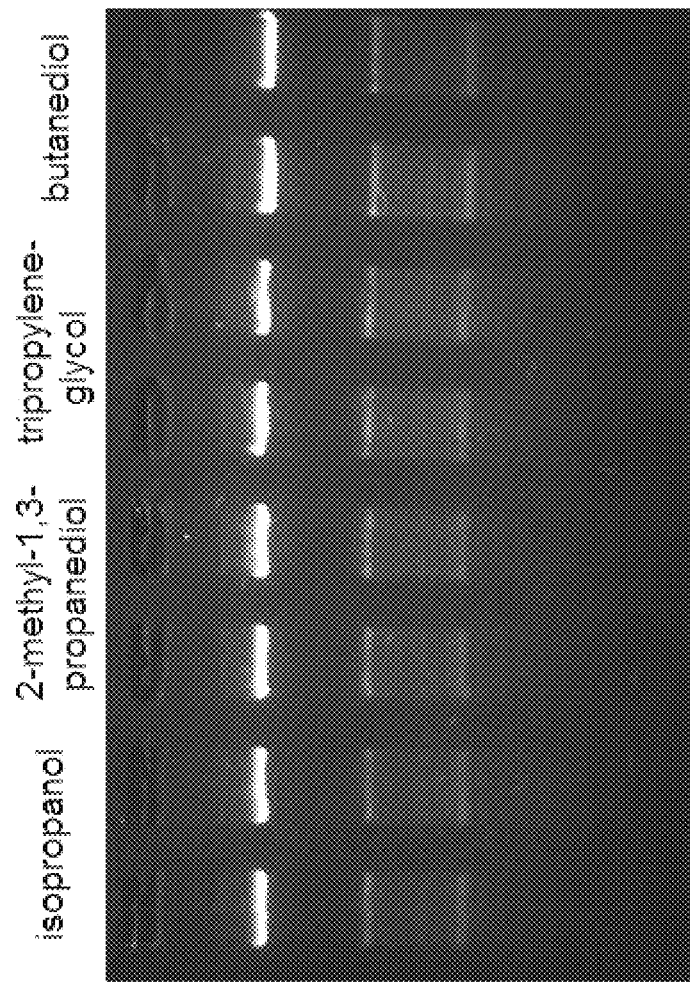

NUCLEIC ACID PREPARATION METHOD

CROSS-REFERENCE TO RELATED APPLICATIONS

This application is a divisional of U.S. Nonprovisional application Ser. No. 13/989,782, filed Aug. 12, 2013, which is a 371 National Phase Application of International Application No. PCT/EP2011/071218 filed Nov. 28, 2011, which claims the benefit of United Kingdom Application No. 1020095.4 filed Nov. 26, 2010 and claims priority to U.S. Provisional No. 61/421,523 filed Dec. 9, 2010, which disclosures are herein incorporated by reference in their entirety.

FIELD OF THE INVENTION

The present invention relates to procedures for processing nucleic acids, kits for processing nucleic acids and other subject matter, in particular to improved preparation of nucleic acid from samples, especially biological samples such as serum and plasma, in a form suitable for nucleic acid amplification, e.g. amplification and detection by quantitative PCR (qPCR), which avoids the use of alcohol for precipitation and alcohol-containing wash buffers, more particularly ethanol and isopropanol-containing wash buffers as commonly employed in nucleic acid preparation. The present invention provides use of polyols, e.g. undiluted or as aqueous compositions, as an alternative to ethanol and/or isoproponal for precipitation and for removing contaminants from extracted nucleic acid ahead of amplification.

BACKGROUND TO THE INVENTION

The isolation of nucleic acids such as, for example, DNA or RNA is an important step in many biochemical and diagnostic procedures. For example, the separation of nucleic acids from the complex mixtures in which they are often found is frequently necessary before other studies and procedures e.g. detection, cloning, sequencing, amplification, hybridisation, cDNA synthesis, studying nucleic acid structure and composition (e.g. the methylation pattern of DNA) etc can be undertaken. The presence of large amounts of cellular or other contaminating material e.g. proteins or carbohydrates, in such complex mixtures often impedes many of the reactions and techniques used in molecular biology. In addition, DNA may contaminate RNA preparations and vice versa. Thus, methods for the isolation of nucleic acids from complex mixtures such as cells, tissues etc. are demanded, not only from the preparative point of view, but also in the many methods in use today which rely on the identification of DNA or RNA e.g. diagnosis of microbial infections, forensic science, tissue and blood typing, genotyping, detection of genetic variations etc. The purification of DNA or RNA from more enriched but still contaminated samples is also desirable, e.g. to purify synthetically prepared nucleic acid material, e.g. to purify PCR products from contaminating salts, excess primers and/or dNTPs.

A range of methods are known for the isolation of nucleic acids, but generally speaking, these rely on a complex series of extraction and washing steps and are time consuming and labourious to perform. Moreover, the use of materials such as alcohols and other organic solvents, chaotropes and proteinases is often involved, which is disadvantageous since such materials tend to interfere with many enzymic reactions and other downstream processing applications.

Thus, classical methods for the isolation of nucleic acids from complex starting materials such as blood or blood products or tissues involve lysis of the biological material by a detergent or chaotrope, possibly in the presence of a protein degrading enzyme, followed by several extractions with organic solvents e.g. phenol and/or chloroform, ethanol precipitation, centrifugations and dialysis of the nucleic acids. The purification of RNA from DNA may involve a selective precipitation with LiCl or a selective isolation with acidic guanidinium thiocyanate combined with phenol extractions and ethanol precipitation. Not only are such methods cumbersome and time consuming to perform, but the relatively large number of steps required increases the risk of degradation, sample loss or cross-contamination of samples where several samples are simultaneously processed.

One approach common in RNA purification, which may be used in conjunction with the solid phase approach is to carry out the lysis of the biological material and the subsequent hybridisation to oligodT in LiCl and LiDS/SDS buffers, thereby avoiding extra steps such as phenol extraction or proteinase-K digestion. The whole direct mRNA isolation takes approximately 15 minutes and since the mRNA is stable for more than 30 minutes in the lysis buffer, this ensures the high quality of the mRNA purified. However, a disadvantage of this method is that mRNA per weight unit of tissue is affected by the amount of tissue used and above a critical threshold of lysed cells, the yield of mRNA decreases.

Another common approach for direct mRNA purification is, to use guanidinium isothiocyanate (GTC) and sarkosyl. A GTC-buffer system is preferred by most researchers due to the ability of this chaotropic salt to inhibit RNases. This may also be used in combination with the magnetic bead approach.

However, the viscosity of cell lysates in 4M GTC is high and the beads are not effectively attracted by the magnet, resulting in an increased risk for DNA contamination, both for beads and other solid phases, and lower yields.

More recently, other methods have been proposed which rely upon the use of a solid phase. U.S. Pat. No. 5,234,809, for example, describes a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, monohydric alcohols (ethanol or isopropanol) and salts are used as precipitants.

Ethanol and/or isopropanol when included in sufficient quantity in an aqueous medium act to precipitate dissolved nucleic acids out of solution and to keep out of solution nucleic acids already in the extra-solution phase. Ethanol and isopropanol may therefore be described as "anti-solvating" agents for nucleic acids. Without being bound by theory, it is believed that the ethanol or isopropanol reduce the amount of free water available to dissolve the nucleic acid. These two monohydric alcohols are therefore used during the processing of nucleic acids to precipitate them (e.g. bind them to a solid support) and/or to keep them from dissolving in the aqueous medium, in the latter case while other procedures are carried out. In any particular workflow, one or a combination of these alcohols may be used to precipitate nucleic acid, to keep nucleic acid precipitated, or both to precipitate nucleic acid and to keep it precipitated.

U.S. Pat. No. 5,705,628 and U.S. Pat. No. 5,898,071 describe methods of isolating nucleic acid fragments using a combination of large molecular weight polyalkylene glycols (e.g. polyethylene glycols) at concentrations of from 7 to 13% with salt in the range of 0.5 to 5M to achieve binding to functional groups on a solid support which acts as a bioaffinity absorbent for DNA.

Although such methods generally speed up the nucleic acid separation process, there are disadvantages associated with basing procedures involving solid phase nucleic acids on current agents for inducing and/or maintaining the precipitated state, for example alcohols (such as ethanol or isopropanol), chaotropes, salts and large molecular weight molecules.

Large molecular weight molecules increase the viscosity of the liquid which reduces the efficiency with which purification protocols can be conducted. In the case of separation of magnetic beads, such large molecules reduce the speed of isolation as the time of contact with the magnet to separate the beads has to be increased. Furthermore, the removal of supernatant in such systems is more difficult in the presence of the large molecular weight molecules.

Chaotropes need to be used at high molarity, resulting in viscous solutions which may be difficult to work with, especially in RNA work. Amplification procedures such as PCR, and other enzyme-based reactions, are very sensitive to the inhibitory or otherwise interfering effects of alcohols and other agents. Moreover, the drying of the nucleic acid pellet which is necessary following alcohol (i.e. ethanol or isopropanol) precipitation and the problems with dissolving nucleic acids, are also known to lead to artefacts in enzyme-based procedures such as PCR. Furthermore, liquids with a high content of ethanol or isopropanol are volatile and flammable, which increases transport and disposal costs for the liquids and hence increases the cost of the overall process.

Since such preparation procedures are now a mainstay of molecular biology, there is a need for improved methods of nucleic acid isolation, and particularly for methods which are quick and simple to perform, which enable good yields to be obtained with minimal losses, and which avoid the use of volatile solvents and chaotropic agents or alcohol precipitation or the use of high levels of salt and/or high molecular weight compounds with high viscosity.

A replacement for alcohol in these known preparation procedures would advantageously function as anti-solvating agent at a final concentration that does not increase the volume of the system in order to work in established automated assays.

It would be desirable to be able to use another agent than those currently used to remove nucleic acids from solution or to keep them out of solution whilst contacting them with a liquid medium. It would be more advantageous to be able to remove nucleic acids from solution, or to keep them out of solution whilst contacting them with a liquid medium, by using an agent which did not involve to the same extent the shortcomings of the agents currently used for these purposes.

SUMMARY OF THE INVENTION

The invention is based in part on an appreciation that polyols are not solvents for nucleic acids and have "anti-solvating" activity in relation to nucleic acids, for example such that monohydric alcohols previously used in processing (e.g. washing) nucleic acids extracted from biological samples such as serum or plasma desired to be out of solution phase can be replaced in whole or in part by a polyol, e.g. undiluted or as an aqueous composition, e.g. a simple aqueous dilution, which need not be eliminated prior to nucleic acid amplification and detection, e.g. by means of qPCR.

In one aspect of the invention, there is provided use of a polyol to cause or facilitate a nucleic acid in solution in an aqueous medium to leave the solution phase by combining the aqueous medium with the polyol, or the use of a polyol to maintain or help maintain nucleic acid out of the solution phase when it is contacted with a liquid by contacting nucleic acid with a liquid comprising a polyol. In one embodiment, therefore, the invention comprises combining a polyol with an aqueous medium in which nucleic acid is dissolved such that nucleic acid comes out of solution, e.g. precipitates or binds to a solid support. In another embodiment, the invention comprises contacting a nucleic acid which is not in the solution phase, e.g. is in the solid phase and/or bound to a solid support, with a liquid comprising a polyol such that the nucleic acid does not enter solution; in this embodiment the liquid may be used for another purpose (another function), e.g. washing the nucleic acid and any bound solid support. The invention therefore includes the use of a liquid comprising a polyol to wash a nucleic acid, for example a nucleic acid bound to a solid support.

A further aspect of the invention resides in a method for processing a nucleic acid, in which method the nucleic acid is exposed to an aqueous medium which includes a polyol in sufficient proportion to induce or facilitate at least a portion of the nucleic acid to adopt (e.g. to enter or, as the case may be, to stay in) an extra-solution phase. The invention includes the use of a polyol to induce or facilitate nucleic acid to enter or, as the case may be, to stay in an extra-solution phase. The extra-solution phase may be a support-bound phase or a precipitate, for example. The support may be or comprise beads, e.g. beads having a silica surface, as in the case of silica-coated magnetic polymer beads.

The nucleic acid may be exposed to an aqueous medium containing the polyol in an amount of at least 40% v/v, e.g. of at least 50% v/v and optionally at least 55% v/v. The nucleic acid may be exposed to an aqueous medium containing the polyol in an amount of not more than 75% v/v.

In embodiments the extra-solution phase is a solid support-bound phase and the polyol is used to induce or facilitate nucleic acid to bind to a solid support, for example an aqueous medium having nucleic acid dissolved therein may be combined with the polyol and the solid support. The polyol which is combined with the other components may be in the form of an aqueous solution thereof. The order in which the combination happens is not critical to the invention: e.g. in one embodiment the polyol is first combined with the nucleic acid-containing medium and the resulting mixture is then combined with the solid support; in another embodiment, the solid support is first combined with the nucleic acid-containing medium and the resulting mixture is then combined with the polyol; in another embodiment, the polyol and the solid support are first combined to form a mixture which is then combined with the nucleic acid-containing medium; in another embodiment the polyol, solid support and nucleic acid-containing medium are combined together at the same time.

In embodiments the extra-solution phase is a solid support-bound phase and the polyol is used to wash nucleic acid bound to a solid support, for example the support-bound nucleic acid may be contacted with an aqueous solution of the polyol.

The binding use may be followed by separating the solid support from liquid and then by the washing use.

In one embodiment, the method of the invention comprises combining an aqueous medium having nucleic acid dissolved therein with a polyol to cause or facilitate the nucleic acid to leave solution, e.g. to form a precipitate or to bind to a solid support. The aqueous medium may be combined with the polyol itself or with a mixture, e.g. an aqueous mixture, which comprises, or is, the polyol.

In another embodiment, the method comprises combining a solid support having nucleic acid bound thereto with a liquid comprising a polyol. The liquid may comprise, or be, a mixture of water and the polyol. The liquid may be used to wash the nucleic acid. A particular implementation of the invention comprises washing a nucleic acid bound to a solid support, comprising contacting the solid support and its bound nucleic acid with a liquid which comprises, or is a polyol/water mixture.

As polyols may be mentioned polyols selected from $C_2$-$C_{10}$ alkanes and alkenes, particularly alkanes, substituted by at least two hydroxy groups and optionally interrupted by 1, 2 or 3 ether linkages.

Nucleic acid processed using a process or use of the invention is usually subjected to one or more further processes, for example amplification, e.g. PCR. It will be appreciated that the precise nature of a chosen washing liquid comprising or consisting of the polyol will be such that satisfactory further processing, for example nucleic acid amplification, e.g. qPCR, can proceed. Effective washing will act adequately to remove undesired contaminants while not itself substantially impeding subsequent nucleic acid processing, e.g. amplification. An important factor in this regard is viscosity of the final buffer for nucleic acid amplification including carried over polyol, and the desirability of low viscosity may lead to the use for example of an aqueous dilution of a polyol for washing, e.g. 60% aqueous v/v 2-methyl-1,3-propanediol has been found an advantageous substitute for a conventional 70% aqueous ethanol medium for washing of nucleic acid captured on silane beads prior to elution of the nucleic acid with an elution buffer.

Even with use of an elution buffer some carry over of the polyol to the nucleic acid amplification mixture is inevitable, but it has been found that this need not necessarily be a concern; with qPCR it has been shown that final washing of extracted bead-bound nucleic acid from a biological sample in accordance with the invention using a liquid comprising a polyol, e.g. an aqueous solution of 2-methyl-1,3-propanediol as above, gives no significant change in determined efficiency of nucleic acid isolation compared with preparation of nucleic acid from such a sample using a conventional procedure employing the same solid support and alcohol-containing wash buffers.

Where the desired isolated nucleic acid is to be derived from a biological sample, washing of nucleic acid on a solid support using a polyol as discussed above may be preceded by nucleic acid extraction and binding to the support using the same lysis/binding buffer for both extraction and binding. Conventionally isopropanol is generally added to such a lysis/binding buffer to facilitate or induce nucleic acid binding to the support, e.g. magnetic beads, whereas the invention in one aspect replaces some or, usually, all of the isopropanol with a polyol. Also it may be possible to substitute polyol for the isopropanol typically added to the lysis/binding buffer The invention includes a method of washing a composition comprising a nucleic acid bound to a solid support, the method comprising contacting the solid support with a polyol. The liquid and the solid support may then be separated.

In a further aspect the invention provides a use of a liquid comprising a polyol, such as a $C_2$-$C_{10}$ polyol, to facilitate precipitation of a nucleic acid from a biological sample onto a solid support, wherein the polyol can be an alkane or alkene substituted by at least two hydroxy groups and optionally interrupted by 1, 2 or 3 ether linkages.

In another aspect the invention provides a method for preparing nucleic acid from a sample for nucleic acid amplification, characterised in that the nucleic acid is not contacted with ethanol or isopropanol and is subjected to least one washing step employing a liquid comprising a polyol to remove contaminants, optionally without requiring a step to specifically remove said polyol prior to amplification.

Another aspect provides the use of a liquid comprising a polyol to carry out a nucleic acid washing step. The nucleic acid washing step is as specified in the methods of the invention.

A further aspect provides the use of a solid support for nucleic acid capture. The nucleic acid capture is performed in a manner specified in the methods of the invention.

In another aspect the invention provides the use of an alcohol-free buffer which can release nucleic acid from cells, organelles or viral particles in a biological sample, in a method of the invention. The alcohol-free buffer is employed as the lysis/binding buffer.

In another aspect the invention provides the use of a liquid comprising a polyol to wash a nucleic acid, optionally bound to a solid support, ahead of nucleic acid amplification or another process, wherein said polyol is not subjected to a specific removal step prior to said amplification. In embodiments, the nucleic acid is separated from the bulk wash liquid before it is subjected to further procedures, but there is not used a removal step corresponding to an air drying step used in the prior art to remove ethanol residue from nucleic acid which has been washed with aqueous ethanol.

The invention also enables alternative kits for nucleic acid preparation to be provided which do not require inclusion or addition of any highly volatile, flammable solvent, especially ethanol, and can be safely transported and stored. Such kits for carrying out nucleic acid preparation comprising a liquid comprising a polyol for nucleic acid washing and one or both of a lysis/binding buffer and a solid support constitute a further aspect of the invention.

One embodiment of present disclosure comprises use of a polyol to induce or facilitate nucleic acid to enter or, as the case may be, to stay in, an extra-solution phase. A polyol, used to induce or facilitate nucleic acid to enter or, as the case may be, to stay in, an extra-solution phase, in some embodiments is a $C_2$-$C_{10}$ polyol which is an alkane or alkene substituted by at least two hydroxy groups and optionally interrupted by 1, 2 or 3 ether linkages. In some embodiments, a polyol used to induce or facilitate nucleic acid to enter or, as the case may be, to stay in, an extra-solution phase, has a flashpoint of at least 50° C., preferably at least 70° C.

In some embodiments, a polyol, used to induce or facilitate nucleic acid to enter or, as the case may be, to stay in, an extra-solution phase, is a polyhydric alkanol. In some embodiments, a polyol, used to induce or facilitate nucleic acid to enter or, as the case may be, to stay in, an extra-solution phase, is a polyhydric alkanol ether comprising 1, 2 or 3 ether linkages.

In some embodiments, a polyol, used to induce or facilitate nucleic acid to enter or, as the case may be, to stay in, an extra-solution phase, is a branched chain polyol. In some embodiments, a polyol, used to induce or facilitate nucleic acid to enter or, as the case may be, to stay in, an extra-solution phase, is a straight chain polyol.

In some embodiments, a polyol, used to induce or facilitate nucleic acid to enter or, as the case may be, to stay in, an extra-solution phase, is a diol. In some embodiments, a polyol, used to induce or facilitate nucleic acid to enter or, as the case may be, to stay in, an extra-solution phase, is a triol.

In some embodiments, a polyol used to induce or facilitate nucleic acid to enter or, as the case may be, to stay in, an extra-solution phase, has from 3 to 9 carbon atoms, optionally 3 to 7 carbon atoms, further optionally 3, 4 or 5 carbon atoms. In one embodiment, a polyol used to induce or facilitate nucleic acid to enter or, as the case may be, to stay in, an extra-solution phase, has 4 carbon atoms.

In some embodiments, a polyol, used to induce or facilitate nucleic acid to enter or, as the case may be, to stay in, an extra-solution phase, comprises: 2-methyl-1,3-propanediol, 2,3-butanediol, 1,2-propanediol or tripropyleneglycol.

In some embodiments comprising the use of a polyol to induce or facilitate nucleic acid to enter or, as the case may be, to stay in, an extra-solution phase, the nucleic acid is exposed to an aqueous medium containing the polyol in an amount of at least 40% v/v; the polyol in an amount of at least 50% v/v; or the polyol in an amount of not more than 75% v/v.

In some embodiments comprising the use of a polyol to induce or facilitate nucleic acid to enter or, as the case may be, to stay in, an extra-solution phase, the extra-solution phase is a solid support-bound phase and the polyol is used to induce or facilitate nucleic acid to bind to a solid support. In some embodiments comprising the use of a polyol to induce or facilitate nucleic acid to enter or, as the case may be, to stay in, an extra-solution phase, an aqueous medium having nucleic acid dissolved therein is combined with the polyol and the solid support. In some embodiments as described in the preceding sentence, the polyol is in the form of an aqueous solution thereof prior to the combining. In some embodiments comprising the use of a polyol to induce or facilitate nucleic acid to enter or, as the case may be, to stay in, an extra-solution phase, the extra-solution phase is a solid support-bound phase and the polyol is used to wash nucleic acid bound to a solid support. In one embodiment, the support-bound nucleic acid is contacted with an aqueous solution of the polyol.

In some embodiments comprising the use of a polyol to induce or facilitate nucleic acid to enter or, as the case may be, to stay in, an extra-solution phase as described above (i.e., wherein, the extra-solution phase is a solid support-bound phase and the polyol is used to induce or facilitate nucleic acid to bind to a solid support, and an aqueous medium having nucleic acid dissolved therein is combined with the polyol and the solid support, and the polyol is in the form of an aqueous solution thereof prior to the combining) is followed by separating the solid support from liquid and then wherein the extra-solution phase is a solid support-bound phase and the polyol is used to wash nucleic acid bound to a solid support; or wherein the support-bound nucleic acid is contacted with an aqueous solution of the polyol. In some embodiments, these steps can be followed by elution of the nucleic acid from the solid support.

In some embodiments, as described above, the solid support comprises beads comprising a silica surface. In some embodiments the beads are further magnetic.

In some embodiments, as described above comprising the use of a polyol to induce or facilitate nucleic acid to enter or, as the case may be, to stay in, an extra-solution phase, the nucleic acid can be further subjected to one or more additional processes, optionally selected from detection, cloning, analysis, sequencing, amplification, study, transfection, hybridisation, cDNA synthesis, studying nucleic acid structure and/or composition (e.g. the methylation pattern of DNA), size separation and chromatography.

In some embodiments, the present disclosure describes a method of washing a composition comprising a nucleic acid bound to a solid support, the method comprising: a) contacting the solid support with a liquid comprising a polyol; and b) separating the liquid and the solid support, wherein the polyol is optionally as defined below or is a permitted combination of: a $C_2$-$C_{10}$ polyol which is an alkane or alkene substituted by at least two hydroxy groups and optionally interrupted by 1, 2 or 3 ether linkages; and/or a polyol that has a flashpoint of at least 50° C., and/or a flashpoint of preferably at least 70° C.; and/or the polyol is a polyhydric alkanol; and/or is a polyol which is a polyhydric alkanol ether comprising 1, 2 or 3 ether linkages; and/or is a branched chain polyol; and/or is a straight chain polyol; and/or is a diol; and/or is a triol; and/or is a polyol having from 3 to 9 carbon atoms, optionally 3 to 7 carbon atoms, further optionally 3, 4 or 5 carbon atoms; and/or is a polyol having 4 carbon atoms; and/or is 2-methyl-1,3-propanediol; and/or 2,3-butanediol; and/or 1,2-propanediol; and/or tripropyleneglycol; and/or the polyol in an amount of at least 40% v/v; and/or the polyol in an amount of at least 50% v/v; and/or the polyol in an amount of not more than 75% v/v.

In some embodiments, the method described immediately above further comprises preparing the composition comprising the nucleic acid bound to the solid support by: a'. contacting a biological sample with the solid support, whereby the nucleic acid binds to the solid support; b'. separating the sample and the solid support; and c'. optionally washing the solid support with an alcohol free wash buffer, preferably lysis/binding buffer employed for said lysis and contacting.

In some embodiments of a method described above the sample comprises or is a biological fluid, cell lysate, physiological buffer or transport medium. In some embodiments, the method described can further comprise: c. after the separating of the liquid and the solid support, contacting the solid support with an elution buffer, whereby the nucleic acid is separated from the solid support; and d. separating the elution buffer and the solid support.

In some embodiments of the method as described above, the solid support comprises beads comprising a silica surface. In some embodiments of the method, the beads are further magnetic.

The term "extra-solution" phase as used herein refers to a phase outside solution, for example a nucleic acid which has been precipitated or become bound to a solid support is in either case in an extra-solution phase.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Throughout this specification, whenever a value is quoted for a variable, the variable quoted is approximate rather than precise. All values of variables mentioned herein are disclosed both as a precise value and an approximate value. As used herein, the terms "approximate" and "about" mean that the numerical value is approximate and small variations would not significantly affect the use and practice of the compositions and methods provided herein. Where a numerical limitation is used, unless indicated otherwise by the context, "about" or "approximate" means the numerical value can vary by ±10%, e.g. ±5% and optionally ±2%, and remain within the scope of the disclosed embodiments.

For the avoidance of doubt, it is hereby stated that the information disclosed earlier in this specification under the heading "Background" is relevant to the invention and is to be read as part of the disclosure of the invention.

BRIEF DESCRIPTION OF THE FIGURES

The invention will be further described below with reference to the following figures:

FIG. 6: Comparison of recovery of nucleic acid from human serum with isopropanol and different polyols. 200 ul serum spiked with 2 µg 50 bp DNA ladder in 300 µl viral lysis/binding buffer were precipitated with 150 µl of precipitation agent and isolated 50 µl Dynabeads SILANE as solid phase support. The beads were washed twice with 500 µl of vNA lysis/binding buffer and twice with 500 µl of 60% 2-methyl-1,3-propanediol and eluted in 100 µl elution buffer at 70° C. for 3 minutes. Eluate were analysed on agarose/ethidium bromide gel (2 lanes for each precipitation agent). Isopropanol (lanes 1 and 2) was used as the standard alcohol precipitation agent and compared to 2-methyl-1,3-propanediol (lanes 3 and 4); tripropyleneglycol (lanes 5 and 6) and butanediol (lanes 7 and 8). All bands show the same intensity, diols are as effective as isopropanoll in precipitating nucleic acids.

DETAILED DESCRIPTION

Figure 1:
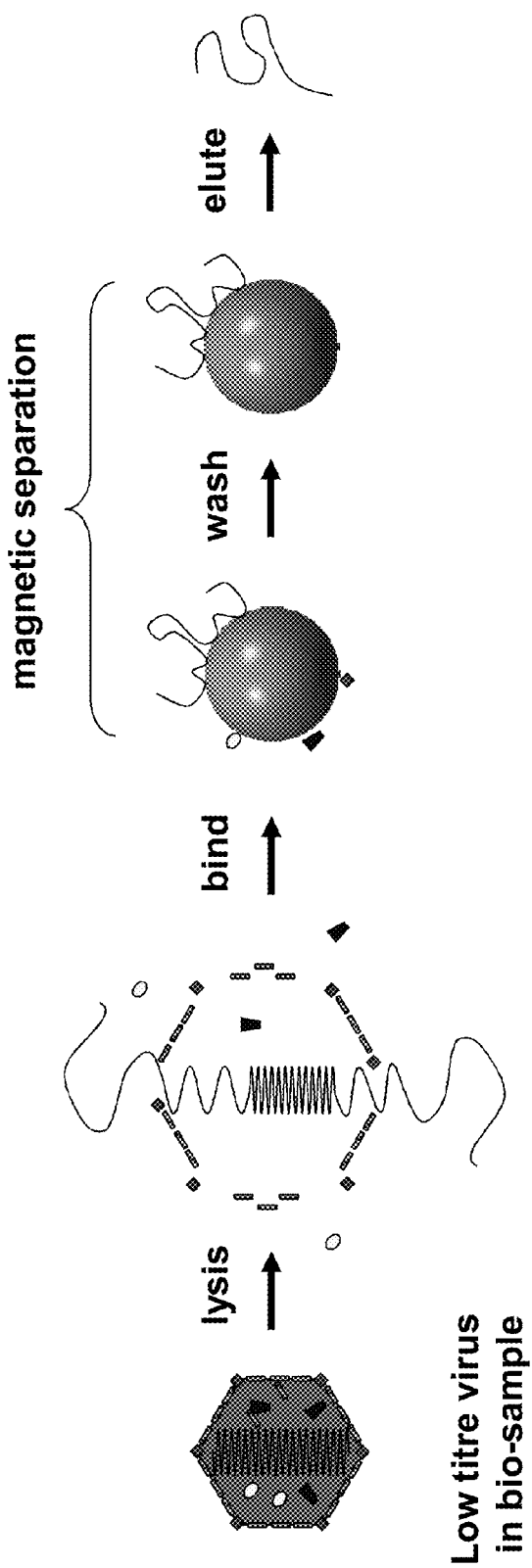
FIG. 1: Protocol steps for conventional preparation of nucleic acid from low titre virus in a biological sample for amplification and detection by qPCR using magnetic beads with a silica-like functionalised surface (available commercially as Dynabeads®. SILANE). This is the protocol enabled by the commercial nucleic acid preparation kit using Dynabeads® MyOne™ SILANE.

The invention provides amongst other things methods for processing a nucleic acid, in which methods the nucleic acid is exposed to an aqueous medium which includes a polyol in sufficient proportion for at least a portion of the nucleic acid to adopt (to enter or remain in) an extra-solution phase.

Thus in one aspect of the invention, there is provided use of a polyol to cause a nucleic acid in solution in an aqueous medium to leave the solution phase by combining the aqueous medium with the polyol, or to maintain nucleic acid out of the solution phase when it is contacted with a liquid by contacting nucleic acid with a liquid comprising a polyol. In one embodiment, therefore, the invention comprises combining a polyol with an aqueous medium in which nucleic acid is dissolved such that nucleic acid comes out of solution, e.g. precipitates and/or becomes associated with a solid support. In another embodiment, the invention comprises contacting a nucleic acid which is not in the solution phase, e.g. is in the solid phase and/or associated with a solid support, with a liquid comprising a polyol such that the nucleic acid does not enter solution; in this embodiment the liquid may be used for another purpose (another function), e.g. washing the nucleic acid and any associated solid support. The invention therefore includes the use of a liquid comprising a polyol to wash a nucleic acid, for example a nucleic acid bound to a solid support.

Also provided by the invention is a composition of matter comprising (i) a liquid which comprises, or consists essentially of, water and a polyol and (ii) a nucleic acid not in solution in the liquid, e.g. bound to a solid support and optionally to a bead.

It will be understood by the skilled reader that it is not necessarily the case that not a single nucleic acid molecule is dissolved by the polyol provided that the process is practically effective for the nucleic acid substantially to enter or stay in the extra-solution phase for its desired further processing, e.g. detection, cloning, analysis, sequencing, amplification, study, transfection, hybridisation, cDNA synthesis, studying nucleic acid structure and/or composition (e.g. the methylation pattern of DNA), size separation, chromatography etc.

In one embodiment, the method comprises combining an aqueous medium having nucleic acid dissolved therein with a polyol to cause the nucleic acid to leave solution, e.g. to form a precipitate or to bind to a solid support. A particular implementation is a method for causing a nucleic acid to bind to a solid support; such a process may comprise forming an aqueous mixture comprising nucleic acid in solution, solid support (e.g. beads) and a polyol. The aqueous medium may be combined with the polyol itself or with a mixture, e.g. an aqueous mixture, comprising the polyol. The mixture may be an aqueous medium consisting of water and the polyol.

In another embodiment, the method comprises combining a solid support having nucleic acid bound thereto with a liquid comprising a polyol. The liquid may comprise, or be, a mixture of water and the polyol. The liquid may be used to wash the nucleic acid. A particular implementation of the invention comprises washing a nucleic acid bound to a solid support, comprising contacting the solid support and its bound nucleic acid with a liquid comprising a polyol/water mixture, for example with an aqueous medium consisting of water and the polyol.

One or both of a process of the invention for causing a nucleic acid to bind to a solid support and washing process of the invention, e.g. employing liquid comprising a polyol in substitution for an alcohol-containing buffer such as 70% ethanol buffer may be a step in isolating a nucleic acid from a biological sample comprising the following:

(a) binding of a nucleic acid in an aqueous composition to a solid support, e.g. beads;
(b) separation of the solid support with bound nucleic acid from the aqueous composition;
(c) washing of the bound nucleic acid to remove contaminants (e.g. lysis agent, proteins, polypeptides or peptides); and if necessary or desired
(d) elution of the nucleic acid from the solid support.

Thus step (a) or step (c) or both may comprise or be a process or use of the invention. The composition used in step (a) may be a mixture comprising nucleic acid in the aqueous phase and free for binding to the solid support. The mixture may be a lysate or extractate resulting from a preliminary step which is a lysis or extraction step for extracting nucleic acid from a starting material, e.g. cells, organelles or viral particles. The eluted nucleic acid may be ready for amplification or other processing.

The invention is not limited as to any further processes to which the nucleic acid is subject after it has been treated by a process or use of the invention. For example, DNA which has been subjected to a use or process of the invention and washed (whether washed by a process of the invention or not) may be further subjected to processes for any one or more of detection, cloning, analysis, sequencing, amplification, study, transfection, hybridisation, cDNA synthesis, studying nucleic acid structure and composition (e.g. the methylation pattern of DNA), size separation, chromatography, amongst other possibilities. Nucleic acid isolation which has involved an activity or product of the invention may therefore be for any purpose, e.g. a diagnostic or analytical purpose, with quantitative detection of amplification by qPCR, e.g. detection of viral nucleic acid.

Figure 2:
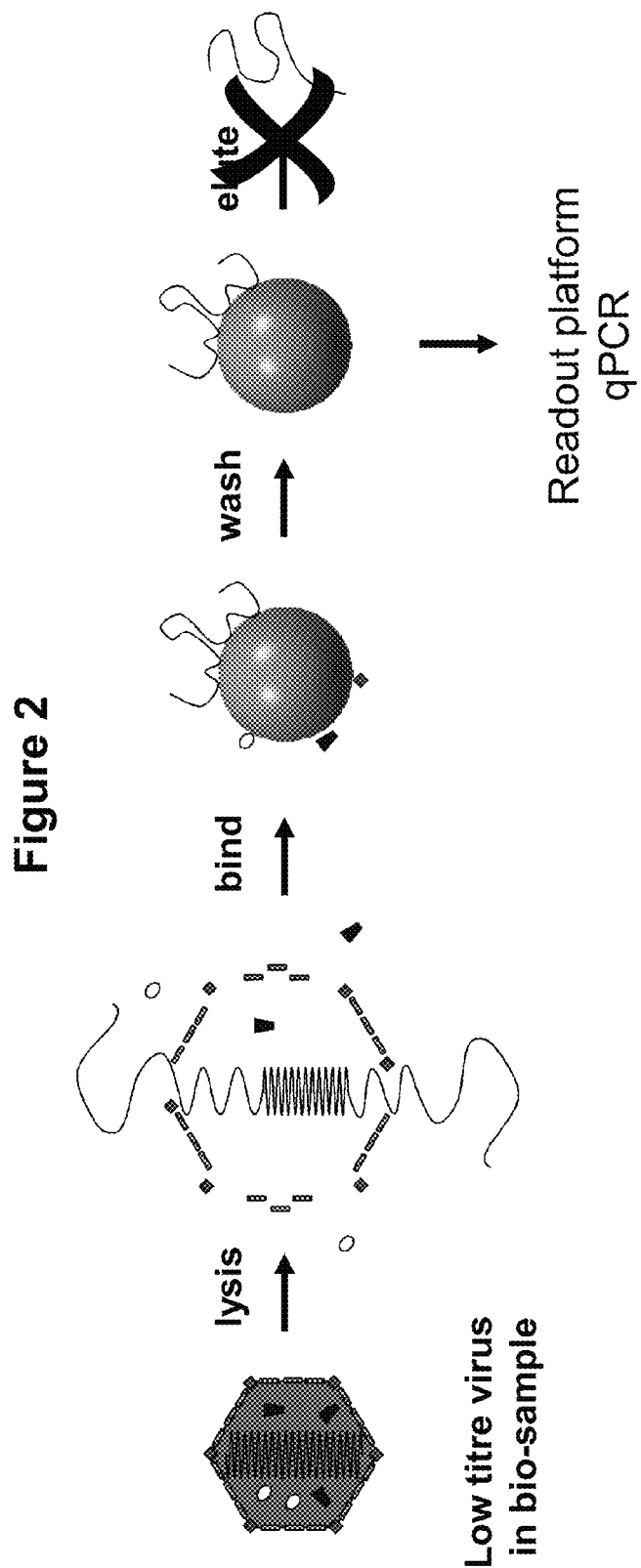
FIG. 2: Alternative bead-in-PCR protocol for preparation and detection of low titre virus nucleic acid from a biological sample in which magnetic Silane beads with captured nucleic acid are not subjected to a nucleic acid heated elution step, but used directly for qPCR.

In many cases, the washed and support-bound nucleic acid will be eluted for its use in one or more subsequent processes. In some instances, however, the washed and support-bound nucleic acid is not eluted. It has been found, for example, that silane beads (i.e. silica-coated beads) with bound nucleic acid may be used directly in an amplification mixture, e.g. for qPCR (see FIG. 2) without elution of the nucleic acid. Where an elution step is required or desired, this may be carried out with a conventional elution buffer such as, for example, an aqueous Tris buffer at pH greater than 7, e.g. a 10 Mm Tris.HCl buffer at pH 8.0.

Any solid support with which nucleic acid associates may be used, e.g. as conventionally employed in nucleic acid isolation from biological samples, but use of beads, especially magnetic beads is preferred. Conveniently and advantageously, it may be chosen to use beads with a silica functionalised surface (silane beads), for example such beads which are available commercially. Particularly favoured are magnetic Dynabeads® MyOne™ SILANE as employed for the examples. These have a high iron oxide content which gives excellent separation in viscous samples such as blood.

The nucleic acid may be DNA or RNA, for example genomic DNA, cDNA, mRNA, rRNA, tRNA, miRNA, or mitochondrial DNA. It may be a plasmid or vector. Such nucleic acid isolation may be for diagnostic purpose with quantitative detection of amplification by qPCR, e.g. detection of viral nucleic acid. It will be understood that the term 'nucleic acid' also extends to non-natural analogues such as PNAs.

The nucleic acid may be derived from (e.g. extracted from) any type of biological sample, e.g. a biological tissue or fluid, for example as fluids may be mentioned serum, plasma, whole blood, urine and cerebrospinal fluid. The biological sample may be one commonly employed for diagnostic assays relying on detection or analysis of an isolated nucleic acid, e.g. viral DNA or RNA. As previously mentioned, the sample subjected to the step of causing nucleic acid to bind to or associate with a solid support may be a cell lysate or virus lysate.

Considering now in more detail a process comprising steps (a)-(c) above, and optionally step (d) above, it will be recalled that such processes may be preceded by preliminary extraction of the nucleic acid by a lysis step. Such lysis and binding of the nucleic acid thereby released to the solid support may employ the same lysis/binding buffer, carried through from the lysis step to the binding step. The lysis/binding buffer typically comprises a chaotrope. The lysis/binding buffer typically comprises a surfactant, for example a non-ionic surfactant, of which poly(oxyethylene)-containing surfactants may be mentioned. The lysis/binding buffer may be any buffer known for this purpose, e.g. with a high concentration of chaotrope (for example a guanidinium salt or urea) and surfactant, e.g. Triton x-100. However, preferred for this purpose is a high detergent, guanidinium isothiocyanate (GTC)-containing buffer such as the lysis/binding buffer supplied by Invitrogen in the Dynabeads® SILANE genomic DNA kit (catalogue No. 370.21D). The lysis step may also use a protease, e.g. proteinase K. The lysis may therefore be performed by combining a cell, a virus or another biological structure with a chaotrope (for example a guanidinium salt or urea), a surfactant (for example a non-ionic surfactant, e.g. a polyoxyethylenic surfactant) and a protease (for example proteinase K).

In the nucleic acid-binding step of a conventional nucleic acid isolation protocol, the lysis/binding buffer is commonly supplemented with isopropanol e.g. 50% isopropanol, or it may be supplemented with ethanol, to facilitate capture of the nucleic acid on the solid support. Such monohydric alcohol supplementation is not excluded by the present invention, provided that (in the context of a process comprising steps (a)-(c) above) a polyol is used in at least one of the nucleic acid binding step (a) and the washing step (c). In any event, a nucleic acid-binding process of the invention comprises combining an aqueous medium comprising nucleic acid and a polyol in the presence of a solid support capable of binding nucleic acid, e.g. by virtue of a silica coating. The polyol is used in an amount sufficient to cause or facilitate binding of the nucleic acid to the solid support. The exact amount cannot be stipulated, since it depends on many variables, including for example the choice of polyol and the identity and amount of other substances in the medium. For example, the inclusion of a monohydric alcohol or a salt (e.g. a sodium or magnesium salt, for example sodium chloride, sodium acetate or magnesium chloride) may reduce the amount of polyol required. In one class of embodiments, additional anti-solvating reagents such as, for example, a salt and/or a monohydric alcohol are not used together with a polyol (not combined with the polyol and other materials). In another class of embodiments, an additional anti-solvating reagent such as, for example, a salt and/or a monohydric alcohol is used together with a polyol (is combined with the polyol and other materials).

The amount of polyol included in the nucleic acid binding medium (i.e. the total liquid phase used in the binding process) is sufficient for nucleic acid to bind to the solid support. The invention includes nucleic acid precipitation processes where no solid support is involved, e.g. where the nucleic acid is precipitated and then recovered from the liquid medium by centrifugation, and in these processes the amount of polyol included in the nucleic acid precipitation medium (i.e. the total liquid phase used in the precipitation process) is sufficient for nucleic acid to precipitate. In embodiments, the sole material used to induce or facilitate binding or precipitation of nucleic acid to the solid support is a polyol, i.e. one or more polyols, e.g. a single polyol. The polyol may be used in an amount sufficient to achieve a final concentration in the binding or precipitation medium of at least 40% by volume of the total binding or precipitation medium, and optionally of at least 50%, 55% or 60% by weight of the total binding or precipitation medium. In some embodiments, the polyol is used in an amount sufficient to achieve a final concentration in the binding or precipitation medium of no more than 75% by volume, e.g. no more than 70% by volume, of the total binding or precipitation medium. For example, the final concentration may be from 40%-75%, e.g. 50%-75%, for example 55%-75% and optionally 60%-75% as in 60%-70%, all percentages being by volume of the total binding or precipitation medium.

After the binding step of above-mentioned steps (a)-(c), the solid support is separated from the aqueous phase, i.e. from the surrounding medium. In embodiments, the solid support comprises magnetic beads and the separating comprises applying a magnetic force to the beads (e.g. bringing together a magnet and the container which contains the aqueous composition and beads) to prevent their free movement and removing the liquid medium, e.g. by pipette. In other embodiments, alternative procedures are used to recover the solid phase, e.g. separating beads by filtration or centrifugation.

After separation of the solid support from the sample in above-mentioned steps (a)-(c) (i.e. separation from the binding medium), the solid-bound nucleic acid is washed. It will be recalled that at least one of and optionally both of steps (a) and (c) use a polyol. In some embodiments a single one of steps (a) and (c) does not involve a polyol.

A nucleic acid washing process of the invention comprises combining a bound or solid phase (precipitate) nucleic acid and a polyol. The polyol may be used on its own or, more commonly, as a mixture with water or with water and other dissolved components e.g. a buffer or a salt or a combination thereof. The polyol may therefore be used as an aqueous medium comprising or consisting of water and the polyol. Where the polyol is in the form of a polyol/water mixture, the amount of the polyol is sufficient to keep the nucleic acid in the bound or solid phase. The exact amount cannot be stipulated, since it depends on many variables, including for example the choice of polyol and the identity and amount of any other substances in the mixture. For example, the inclusion of a monohydric alcohol may reduce the amount of polyol required. In one class of embodiments, additional anti-solvating reagents such as, for example, a monohydric alcohol are not included in the polyol/water mixture. In another class of embodiments, an additional anti-solvating reagent such as, for example, a monohydric alcohol is included in the polyol/water mixture.

The amount of polyol included in the washing medium (i.e. the total liquid phase used in the washing process) is sufficient for nucleic acid to remain bound to the solid support. The invention includes nucleic acid washing processes where no solid support is involved, e.g. where the nucleic acid is precipitated and then recovered from the liquid medium by centrifugation, after which the precipitate is contacted with a washing liquid from which it may in turn be separated by centrifugation; in these processes amount of polyol included in the washing medium (i.e. the total liquid phase used in the washing process) is sufficient for nucleic acid to remain as a precipitate. In embodiments, the sole material used to maintain nucleic acid in the bound or precipitated state is a polyol, i.e. one or more polyols, e.g. a single polyol. The polyol may be used in an amount sufficient to achieve a final concentration in the washing medium of at least 40% by volume of the total washing medium, and optionally of at least 50%, 55% or 60% by weight of the total washing medium. In some embodiments, the polyol is used in an amount sufficient to achieve a final concentration in the washing medium of no more than 75% by volume, e.g. no more than 70% by volume, of the total washing medium. For example, the final concentration may be from 40%-75%, e.g. 50%-75%, for example 55%-75% and optionally 60%-75% as in 60%-70%, all percentages being by volume of the total washing medium.

One washing medium which may be used is aqueous 2-methyl-1,3-propanediol in which the diol is in an amount of at least 60 volume %, and particularly is 60 volume % aqueous 2-methyl-1,3-propanediol.

Figure 3:
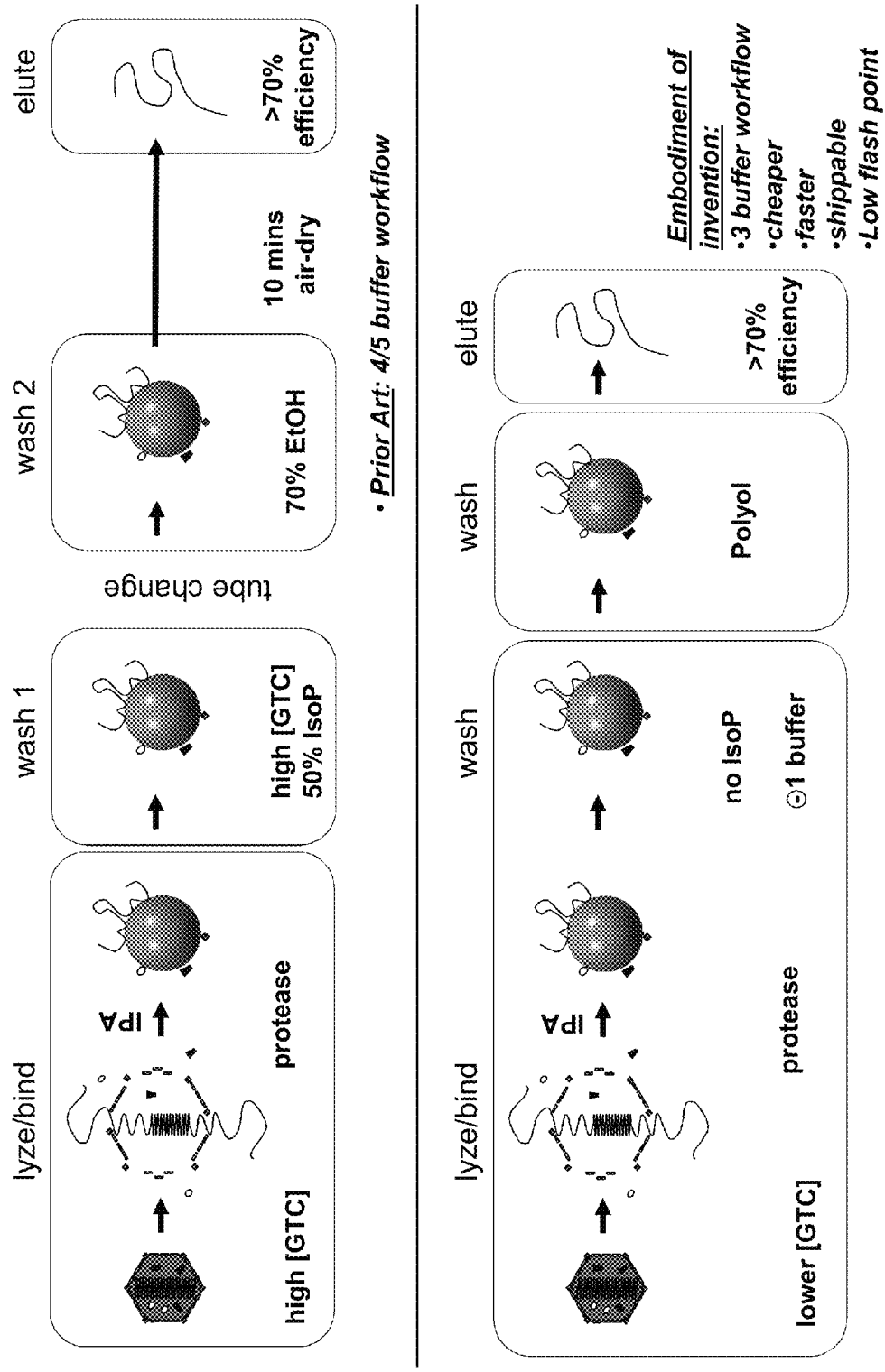
FIG. 3: Comparison of a conventional workflow for viral nucleic acid preparation with a workflow for such nucleic acid preparation employing a wash step with an aqueous polyol solution. Agent X is for example aqueous 60% v/v 2-methyl-1,3-propanediol and replaces conventional use of 70% Ethanol for wash 2. GTC=guanidinium isothiocyanate. The protease is Proteinase K.

In embodiments, an initial washing of the nucleic acid may preferably employ solely a lysis/binding buffer of the same composition as previously used in a binding step and optionally carried over into the binding step from a lysis step. In these embodiments of washing procedures falling within the invention, the procedures comprise subsequent washing with a liquid comprising polyol as just described, e.g. a polyol/water mixture. In a prior art process where an ethanolic washing medium (e.g. 70% aqueous ethanol) is used to wash beads with bound nucleic acid following their washing with a lysis/binding buffer, a first step of the ethanolic wash comprises suspending the beads in the ethanolic medium and transferring the suspended beads to a clean container (normally a clean tube), whilst the washed beads are air-dried (thus removing ethanol) before elution or other processing. At least in some embodiments, subsequent washing with a liquid comprising polyol rather than an ethanol wash buffer brings advantage in that there is both no need for a tube change or removal of the polyol ahead of nucleic acid elution and/or amplification (see FIG. 3). FIG. 3 is a comparison between (i) a conventional workflow (upper workflow entitled "4/5 buffer workflow") for viral nucleic acid preparation, using 50% isopropanol ("IsoP") and 70% ethanol ("EtOH") to wash bead-bound nucleic acid, and (ii) a workflow of an embodiment of the invention (lower workflow entitled "3 buffer workflow") for such nucleic acid preparation employing a wash step with an aqueous polyol solution. Polyol is for example aqueous 60% v/v 2-methyl-1,3-propanediol and replaces conventional use of 70% Ethanol for wash 2. GTC=guanidinium isothiocyanate. The protease is typically Proteinase K.

Thus, in a further aspect, the invention provides the use of a solid support in the separation of a nucleic acid from a biological sample, after a lysis step, by contacting the sample with the solid support under conditions whereby the nucleic acid becomes bound to the support, separating the sample and the solid support, and then washing the nucleic acid on the solid support, wherein said washing includes washing with a liquid comprising a polyol, preferably preceded by initial washing with alcohol free lysis/binding buffer of the same composition used for said lysis and contacting. The washing may include initial washing with alcohol free lysis/binding buffer used for the lysis and contacting.

The polyol employed will be liquid at room temperature. It may be a polyol having 2, 3, 4, 5, 6, 7, 8, 9 or 10 carbon atoms and which is an alkane or alkene substituted by at least two hydroxy groups and optionally interrupted by 1, 2 or 3 ether linkages; in particular embodiments, the polyol is a $C_2$-$C_{10}$ alkane substituted by at least two hydroxy groups and optionally interrupted by 1, 2 or 3 ether linkages. It may be a branched chain or straight chain polyol. The polyol may have from 3 to 9 carbon atoms, optionally 3 to 7 carbon atoms, further optionally 3, 4 or 5 carbon atoms.

Particular polyols have exactly two hydroxy groups, i.e. they are diols. Some other polyols have exactly three hydroxy groups, i.e. they are triols. The polyols may be polyhydric alkanols (alkanepolyols). The polyols may be polyhydric alkanols (alkanepolyols) interrupted by 1, 2 or 3 ether linkages.

In some embodiments, the alkanepolyol or alkenepolyol has at least one substituent additional to the hydroxy groups, e.g. it may be substituted by one or more halogens, typically selected from F and Cl. More usually, the alkane or alkene, in either case optionally interrupted by 1, 2 or 3 ether linkages, is substituted solely by hydroxy groups.

In selecting a polyol, it will be preferable to choose a polyol with a flash point of at least 50° C., preferably at least 70° C. It will also be preferable to avoid polyols which will affect pH, e.g. a polyol with an amino group such as amino-2-methyl-1,3-propanediol. Having regard further to viscosity consideration (high viscosity is undesirable), $C_3$ or $C_4$ linear or branched polyols are preferred and it may be found preferable or essential to employ an aqueous composition, e.g. an aqueous solution. Such a composition may comprise at least about 40% v/v of the polyol, more preferably at least 50% v/v of the polyol, e.g. at least 55% v/v or at least 60% v/v of the polyol. It may comprise not more than 90% v/v of the polyol, not more than 80% v/v of the polyol, or not more than 75% or 70% v/v of the polyol. Thus the polyol may be provided in aqueous composition at a concentration of, for example, at least 40% v/v and not more than 80% v/v.

The viscosity of the composition is preferably below 50 Centipoises or mPa s at 4° C. and atmospheric pressure, more preferably below 25 Centipoises at 4° C., most preferably between 1 and 20 Centipoises, 1 and 10 Centipoises, 1 and 5 Centipoises or 1 and 3 Centipoises.

Example polyols include 1,2-ethanediol, 1,2-propanediol, 2-methyl-1,3-propanediol, 1,3-butanediol, 2,3-butanediol, 1,4-butanediol, 2,4-pentanediol, 2,5-hexanediol, glycerol (propane-1,2,3-triol), triethyleneglycol ($HOC_2H_4OC_2H_4OC_2H_4OH$), tetraethyleneglycol, and sorbitol. Particularly favoured polyols are 2-methyl-1,3-propanediol, 2,3-butanediol, 1,2-propanediol and tripropyleneglycol ($HO[CH(CH_3)CH_2O]_3H$). The more viscous polyols such as, for example, glycerol and sorbitol are not so desirable because they detract from ease of processing.

The polyol may be provided as an aqueous solution, meaning that the polyol combined with dissolved nucleic acid in a process of the invention for causing or facilitating precipitation or binding of a nucleic acid may be in the form of an aqueous solution, and that a polyol wash medium used in a washing process of the invention may be an aqueous solution. Especially to be mentioned is an aqueous dilution of 2-methyl-1,3-propanediol. In order to function to induce or facilitate nucleic acid to enter or remain in a precipitated or bound state in the absence of another agent to perform the same function, it has been found suitable for aqueous 2-methyl-1,3-propanediol to contain the diol in an amount of from 55%-70%, e.g. 60%; concentrations higher than necessary for good performance are economically disadvantageous. Such polyol solutions satisfy the desired requirements of function to permit efficient nucleic acid isolation without viscosity problems and have a high flash point (are non-volatile/non-flammable) at normal temperatures and hence can be included in shippable kits as non-hazardous components.

Indeed as noted above an important advantage of applying the methodology of the invention and avoiding use of alcohol-containing wash buffers such as 70% ethanol wash buffer is that non-hazardous shippable kits can consequently be provided for nucleic acid isolation. Thus a further important aspect of the invention is a kit which comprises a washing liquid comprising a polyol as discussed above and one or both of a solid support and an alcohol free lysis/binding buffer as also discussed above. Such a kit may further comprise an elution buffer. The kit may be a diagnostic kit which also includes oligonucleotide primers for amplification of an isolated nucleic acid of interest, e.g. a viral nucleic acid or part thereof and/or an oligonucleotide probe which can be used to detect a sequence of interest in isolated nucleic acid.

The following non-limiting examples illustrate the invention.

EXAMPLES

Example 1

Comparison of Recovery Detected by qPCR of DNA of M13 Virus Spiked into Serum, Plasma or Blood Using a Conventional Protocol for Nucleic Acid Isolation and Modified Protocol Using Alcohol-Free Wash Buffers Methods The conventional protocol used the Dynabeads® SILANE viral NA kit (Invitrogen catalogue No. 370.11D) as supplied for isolation of viral DNA/RNA from serum or plasma using Dynabeads® MyOne™ SILANE as detailed below.

Conventional Protocol

The protocol described below can be applied for isolation of viral DNA/RNA from 200 µl of serum/plasma using 50 µl (2 mg) Dynabeads® MyOne™ SILANE. The protocol can be scaled up or down to suit specific needs (sample volumes, elution volumes etc).

(i) Preparing the Buffers

Washing Buffer 1 (viral NA) and Washing Buffer 2 (viral NA) are supplied as concentrates. To obtain working solutions, isopropanol/ethanol is added to the two buffers as indicated on the respective labels.

Note: The Lysis/Binding Buffer (viral NA) and the concentrated stock solutions of Washing Buffer 1 (viral NA) will form a precipitate upon storage at temperatures below 15° C. Dissolve by gentle warming on a roller (37° C., 1 hr), and place at room temperature prior to use.

Prior to first time use, add 45 ml isopropanol to each of the two supplied bottles of Washing Buffer 1 (viral NA) to obtain a working solution.

Prior to first time use, add 70 ml ethanol to the bottle of Washing Buffer 2 (viral NA) to obtain a working solution.

Proceed with isolation of viral DNA/RNA as described below.

(ii) Isolation of Viral DNA/RNA

1. Add 50 µl Proteinase K (20 mg/ml) to an empty tube, then add 200 µl serum/plasma and mix by gently tapping the tubes.
2. Add 300 µl Lysis/Binding Buffer (viral NA). Mix by inverting the tubes 4-6 times and incubate at room temperature for 5 minutes.

Note: Proteinase K should not be added directly into Lysis/Binding Buffer (viral NA) without serum/plasma.

Note: The vial containing Dynabeads® MyOne™ SILANE should be resuspended (e.g. vortex) to a homogenous suspension prior to use. Leave the vial on a roller until use.

3. Add 150 µl isopropanol. Then add 50 µl resuspended Dynabeads® MyOne™ SILANE suspension to the mixture from step 2. Mix and incubate on a roller at room temperature for 10 minutes.
4. Place the tube on a magnet and let the Dynabeads® collect at the magnet for 2 minutes (or until the supernatant is clear). Remove the supernatant by using a pipette.
5. Remove the magnet and add 850 µl Washing Buffer 1 (viral NA). Resuspend the Dynabeads® by inverting the tubes or pipetting up and down 3-4 times.
6. Place the tube on the magnet and let the Dynabeads® collect at the magnet for 2 minutes (or until the supernatant is clear). Remove the supernatant.
7. Repeat steps 5 and 6.
8. Remove the magnet and add 450 µl Washing Buffer 2 (viral NA). Resuspend the Dynabeads® by pipetting. Transfer the resuspended bead-solution to a clean tube.
9. Place the tube on the magnet and let the Dynabeads® collect at the magnet for 2 minutes (or until the supernatant is clear). Remove the supernatant.
10. Repeat steps 8 and 9. (A second change of tube is not required.) Make sure that all buffer is completely removed in this last washing step. (Tip: While still on the magnet, tap the tube/magnet on the table to collect the last drop at the bottom of the tube. Use a small pipette tip and make sure that no droplets are left on the tube wall.) Leave the tube on the magnet and let the bead-pellet dry at room temperature for 10-15 minutes.
11. Remove the magnet and add 100 µl Elution Buffer (viral NA). Resuspend the Dynabeads® by pipetting and incubate at 70° C. for 3 minutes.
12. Resuspend the Dynabeads® by gently tapping the tubes. Place the tube on the magnet and let the Dynabeads® collect at the magnet for 2 minutes (or until the supernatant is clear).
13. Transfer the supernatant containing the purified viral DNA/RNA to a clean tube.

Modified Protocol Using Monohydric Alcohol-Free Wash Buffers

The protocol above was modified by substituting the 70% ethanol wash buffer 2 by an aqueous solution of 60% v/v 2-methyl-1,3-propanediol. Lysis/binding buffer (Lysis/Binding Buffer (viral NA) without addition of 50% isopropanol was used as wash buffer 1 without subsequent change of tube for washing with wash buffer 2. The drying step prior to elution was also not required (see FIG. 3).

A detailed isolation protocol (in this case for isolating virus from serum samples) for a polyol wash buffer is as follows:

1. Begin with 200 µl serum samples (containing target virus).
2. Add 50 µl Proteinase K (20 mg/ml) to the serum. Briefly vortex.
3. Add 300 µl Lysis/Binding Buffer (370.21 D), mix and incubate at ambient room temperature for 5 min.
4. Add 150 µl isopropanol. Then add 50 ul resuspended beads (SILANE 370.02D). Mix by shaking and incubate on a roller at ambient room temperature for 10 min.
5. Place the tube on the magnet and let the beads collect at the magnet for 2 min. Remove the supernatant by using a pipette.
6. Remove the magnet. Add 500 µl Lysis/Binding buffer and resuspend the beads. Repeat steps 5+6 (=two washes with Lysis/Binding buffer).
7. Place the tube on the magnet and let the beads collect at the magnet for 2 min. Remove the supernatant by using a pipette.
8. Remove the magnet. Add 500 µl 60% 2-methyl-1,3-propanediol and resuspend the beads. Repeat steps 7+8 (=two washes with 60% 2-methyl-1,3-propanediol).
9. Place the tube on the magnet and let the beads collect at the magnet for 2 min. Remove the supernatant.
10. Remove the magnet and add 100 µl Elution Buffer (10 mM Tris.HCl pH 8.0). Resuspend the beads by vortexing for 20 sec and incubate at 70° C. for 3 min.
11. Resuspend the beads by quick vortex (10 sec). Place the tube on the magnet and let the beads collect at the magnet.
12. Transfer the supernatant containing the purified viral NA to a clean tube ready for downstream application.

The above example protocol for bench-top use can be readily adapted to automated platforms.

Samples

200 µl of each of serum, plasma and blood from the same donor was spiked with $1.37 \times 10^4$ M13 virus particles. Triplicate nucleic acid preparations were carried out for each sample (blood with and without tube change) using the conventional protocol employing alcohol containing wash buffers and the modified protocol employing the alcohol-free, shippable buffer set. Recovered M13 plasmid was determined by triplicate qPCR using the eluate obtained by use of the 100 μl of elution buffer. [Read out assay AB1 7500 instrument plus TaqMan probe. MM=IVGN Patimum qPCR supermix UDG kit, cat no. 11730-025, lot 483683]; 5 μl eluate into 25 μl of PCT mix (so 685 copies if 100% extraction efficiency).

Results

Figure 4A:
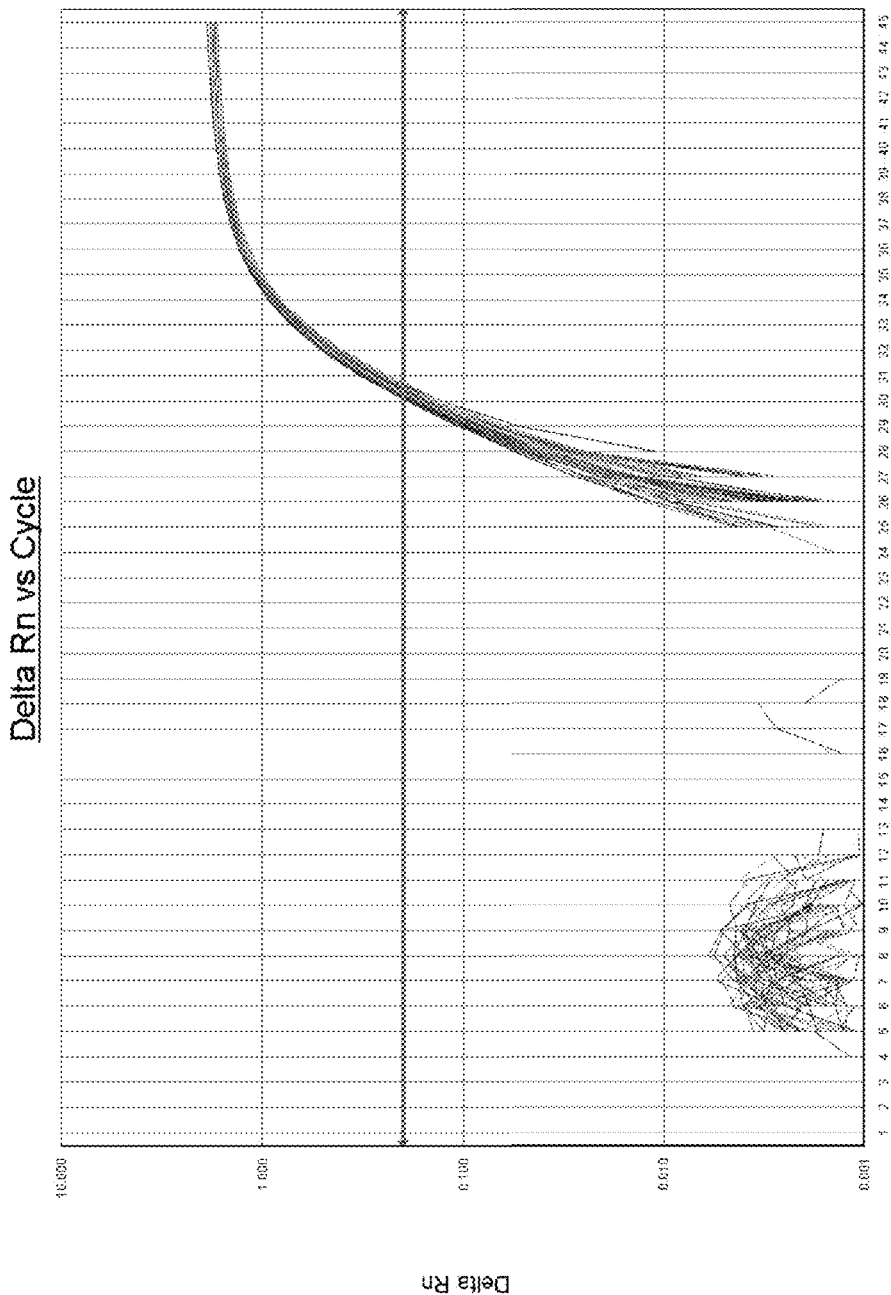
FIGS. 4a and 4b: Comparison of recovery detected by qPCR of M13 plasmid DNA spiked into serum, plasma or blood using a conventional protocol for nucleic acid preparation as shown in FIG. 3 with conventional wash buffers containing alcohol (50% isopropanol in wash buffer 1; 70% ethanol in wash buffer 2) and a modified protocol according to the invention in which wash buffer 1 is simply alcohol-free lysis/binding buffer and buffer 2 is an aqueous 60% v/v 2-methyl-1,3-propanediol. Data was collected for triplicate extractions for each sample type (serum, plasma, blood without a tube change and blood with a tube change) with triplicate qPCR per extraction. The resulting data from 72 amplification curves is shown.
Figure 4B:
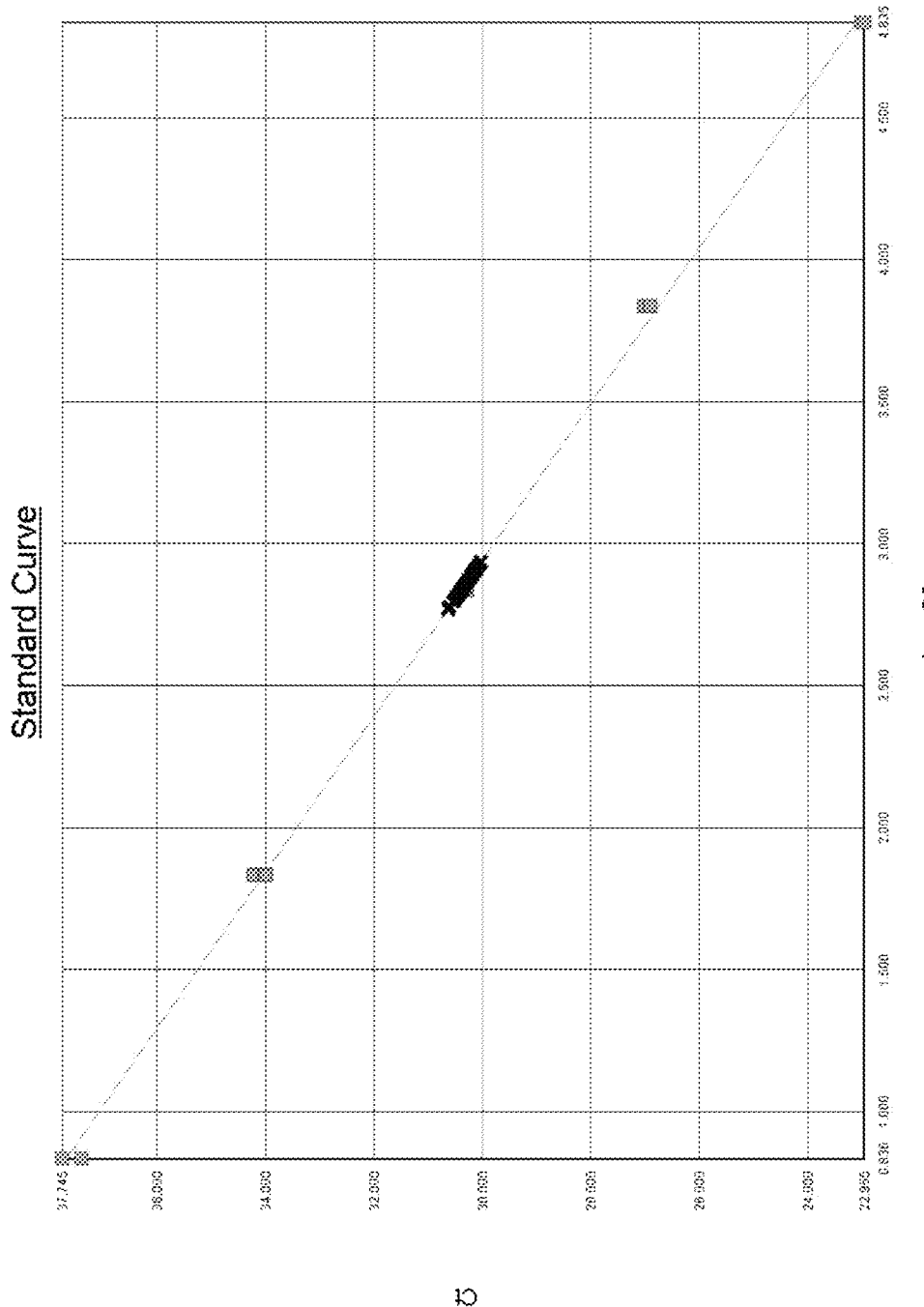

The resulting 72 amplification curves were compared as shown in FIG. 4. This shows that regardless of the buffer chemistry used or the sample type, the isolation efficiency of the viral nucleic acid was unchanged.

Example 2

Comparison of Recovery Detected by qPCR of Viral Nucleic Acid (vNA) from Human Serum with High, Medium or Low Viral Titre Using a Conventional Protocol for Nucleic Acid Preparation and a Modified Protocol Using Alcohol-Free Wash Buffers The same protocols for nucleic acid isolation were used as in Example 1 with 200 μl human serum samples containing M13 at low titre (137 virions), medium titre (6.65e3 virions) and high titre (1.37e6 virions). The modified protocol was also tested with two different concentrations of tripropyleneglycol in aqueous solution (in the range 50 to 70% v/v). Ct values (no of cycles to exceed a threshold fluorescence were compared). By comparison to a standard curve, the percent extraction efficiency for the viral nucleic acid was determined [(number of copies of vNA/number of copies of vNA in sample)×100].

Results

Figure 5:
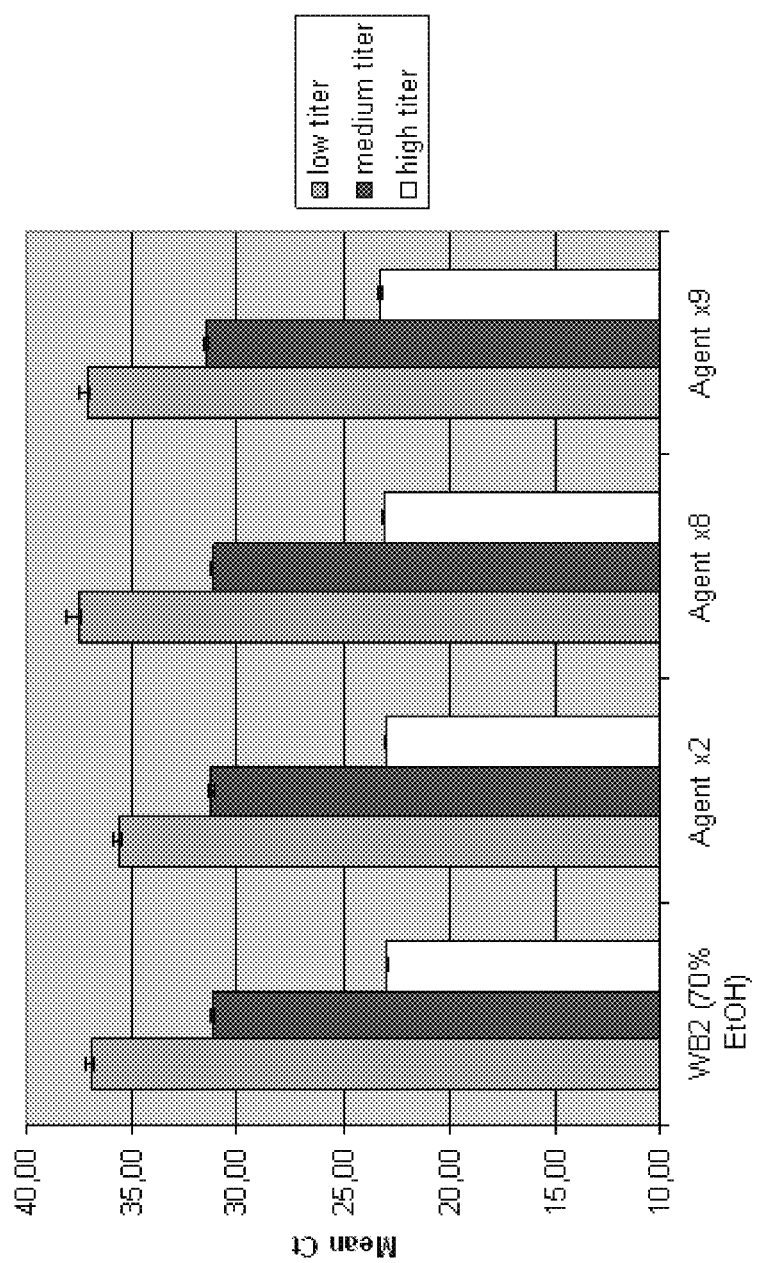
FIG. 5: Comparison of recovery of viral nucleic acid from human serum with high, medium or low viral titre using the same conventional preparation protocol with qPCR and a modified protocol according to the invention in which alcohol-free lysis/binding buffer is used for the first wash and the 70% ethanol wash buffer 2 (WB2) is substituted by aqueous 60% v/v 2-methyl-1,3-propanediol (agent x2) or an aqueous dilution of 50 to 70% v/v tripropyleneglycol (agents x8 and x9). Low titre=137 virions (viral particles) spiked into 200 µl serum. Medium titre=6.65e3 virions spiked into 200 µl serum. High titre=1.37e6 virions spiked into 200 µl serum. Mean Ct equates with number of cycles to exceed a threshold fluorescence. Lower Ct or comparable Ct to the control (WB2=70% ethanol wash buffer) indicates equivalent or better extraction efficiency.

The results are shown in FIG. 5. The modified protocol in which 70% ethanol was replaced with either a 60% solution of 2-methyl-1,3-propanediol or a solution of tripropyleneglycol resulted in comparable or better performance to the control. All the isolations were greater than 70% efficient.

Example 3

Testing of $C_2$-$C_6$ Polyols as Substitute for 70% Ethanol in a Modified Nucleic Acid Isolation Protocol The following linear and branched chain polyols, all liquid at room temperature, were tested in substitution for 70% ethanol wash buffer 2 for M13 nucleic acid isolation from human serum using a modified protocol as described above. Tests were carried out using aqueous solutions with a view to obtaining a suitable low viscosity with retention of efficiency of viral nucleic acid isolation.

2C Compounds:
　1,2 ethanediol (ethylene glycol)
3C Compounds:
　1,2 propanediol
　1,3 propanediol
4C Compounds
　2-methyl-1,3-propanediol
　1,3 butanediol
　1,4 butanediol
　2,3 butanediol
5C Compounds
　2,4 pentanediol
6C Compounds
　2-methyl-2,4-pentanediol
　2,5 hexanediol Results These tests confirmed 2-methyl-1,3-propanediol, 2,3-butanediol, 1,2-propanediol and tripropyleneglycol as favoured polyols able to satisfy all the desired requirements in aqueous solution: desired functionality with low viscosity, liquid at room temperature and non-volatile (non-flammable) for transport. Having regard also to cost, particularly favourable for use was found to be 2-methyl-1,3-propanediol at 60-70% v/v. (2-methyl-1,3-propanediol has melting point −91° C., boiling point 123° C. and a flash point of 100° C.).

2,3-butane-2,3-diol was also found to be useable at 60-70%.

Tripropylene glycol has 9C arranged as 3 groups of 3C linked by 2 further oxygen ether links and may be viewed as a polymer analogue of 2-methyl-1,3-propanediol. It was found to be effective at 50-70%.

1,2-propanediol was found to be effective but although it has a lower molecular weight, the active concentration for use was found to be higher with consequent higher viscosity.

The other polyols tested tended to work less well and/or give poorer viscosity characteristic.

Example 4

Precipitation of Nucleic Acid with Polyols in Comparison to Isopropanol

200 μl serum were spiked with 2 μg 50 bp DNA ladder and 300 μl viral lysis/binding buffer was added.

To this sample 150 μl of precipitation agent and 50 μl Dynabeads SILANE as solid phase support was added.

The beads were washed twice with 500 μl of vNA lysis/binding buffer and twice with 500 μl of 60% 2-methyl-1,3-propanediol and eluted in 100 μl elution buffer at 70° C. for 3 minutes.

Eluate were analysed on agarose/ethidium bromide gel (2 lanes for each precipitation agent).

Isopropanol was used as the standard alcohol precipitation agent and compared to
　2-methyl-1,3-propanediol;
　tripropyleneglycol; or
　butanediol.

Results

As FIG. 6 shows, diols are as effective as isopropanol in precipitating nucleic acids.

The invention claimed is:

1. A composition comprising:
　(i) a polyol or a liquid comprising a polyol, and
　(ii) a nucleic acid, wherein the nucleic acid is not dissolved in the polyol or the liquid comprising the polyol, wherein the polyol is 2-methyl-1,3-propanediol, 2,3-butanediol, or tripropylene glycol.

2. The composition of claim 1, wherein the nucleic acid is bound to a solid support.

3. A kit comprising a polyol or a liquid comprising a polyol, wherein the polyol is 2-methyl-1,3-propanediol, 2,3-butanediol, or tripropylene glycol, at least one of a lysis buffer or a binding buffer, and a solid support.

4. The composition of claim 1 or the kit of claim 3, wherein the solid support is a bead comprising a silica surface.

5. The composition or kit of claim 4, wherein the solid support is a magnetic bead.

6. A method of washing a solid support, comprising:
　a. providing a solid support, wherein a nucleic acid is bound to the solid support;

b. contacting the solid support with a liquid comprising a polyol, wherein the polyol is 2-methyl-1,3-propanediol, 2,3-butanediol, or tripropylene glycol; and
c. separating the liquid and the solid support.

7. A method of washing a solid support, comprising:
a. contacting a biological sample comprising a nucleic acid with the solid support, whereby the nucleic acid binds to the solid support;
b. contacting the solid support with a liquid comprising a polyol, wherein the polyol is 2-methyl-1,3-propanediol, 2,3-butanediol, or tripropylene glycol; and
c. separating the liquid and the solid support.

8. The method of claim 7, further comprising washing the solid support with an alcohol free wash buffer.

* * * * *